United States Patent [19]

Park et al.

[11] Patent Number: 5,101,050
[45] Date of Patent: Mar. 31, 1992

[54] PROCESS FOR THE PRODUCTION OF AROMATIC ANHYDRIDES AND AROMATIC ESTERS WITH SUPERIOR COLOR PROPERTIES

[75] Inventors: Chang M. Park; Ronald Coates; Juergen K. Holzhauer, all of Naperville, Ill.; John V. Peterson, Portage, Ind.

[73] Assignee: Amoco Corporation, Chicago, Ill.

[21] Appl. No.: 606,603

[22] Filed: Oct. 31, 1990

Related U.S. Application Data

[63] Continuation-in-part of Ser. No. 443,564, Nov. 29, 1989, abandoned.

[51] Int. Cl.$^5$ .................. C07D 307/77; C07C 67/00; C07C 67/48
[52] U.S. Cl. .................. 549/245; 549/250; 560/77; 560/78; 585/830
[58] Field of Search .................. 549/245, 250; 560/77, 560/78; 585/830

[56] References Cited

U.S. PATENT DOCUMENTS 4,886,901 12/1989 Holzhauer et al. .................. 560/77

FOREIGN PATENT DOCUMENTS 1948374 4/1970 Japan.

*Primary Examiner*—José G. Dees
*Assistant Examiner*—D. D. Cam
*Attorney, Agent, or Firm*—Thomas E. Nemo; William H. Magidson; Ralph C. Medhurst

[57] ABSTRACT

A process for the production of aromatic esters or aromatic anhydrides with improved color properties is disclosed. This process comprises treating the aromatic ester or aromatic anhydride with an activated boric acid followed by fractionation.

19 Claims, No Drawings

PROCESS FOR THE PRODUCTION OF AROMATIC ANHYDRIDES AND AROMATIC ESTERS WITH SUPERIOR COLOR PROPERTIES

This application is a continuation-in-part application of U.S. Ser. No. 443,564 filed on Nov. 29, 1989.

BACKGROUND OF THE INVENTION

1. Field of the Invention

This invention relates to the production of aromatic anhydrides and aromatic esters having superior color properties. More particularly this invention relates to trimellitic anhydride (TMA) and dimethyl-2,6-naphthalenedicarboxylate (DM-2,6-NDC); and the preparation of high purity TMA from trimellitic acid (TMLA) and the preparation of high purity DM-2,6-NDC. The invention has particular applicability when the trimellitic acid has been produced by the oxidation of a 1,2,4-aliphatic-substituted benzene with molecular oxygen in the liquid phase and in the presence of a heavy metal catalyst.

2. Background

Aromatic anhydrides and aromatic esters are useful intermediates for the production of a wide variety of materials and compositions such as resins, polymers, health related products, etc. Trimellitic anhydride, which is made from trimellitic acid, and dimethyl-2,6-naphthalenedicarboxylate, which is conveniently prepared from 2,6-naphthalenedicarboxylic acid, are two such useful intermediates.

Trimellitic acid, the 1,2,4-benzene tricarboxylic acid, is useful as an intermediate in the production of quality plasticizers and polyester resins. For these applications, in which trimellitic acid is esterified with a monohydric or a polyhydric alcohol, the evolution of water as an esterification by-product together with the attendant difficulty of eliminating water from esterification reaction mixtures favors the desirability of employing trimellitic acid as the anhydride rather than as the acid. Resins and plasticizers may further require a trimellitic anhydride which is relatively free from color bodies and also free from the heavy metals employed as catalysts for the air oxidation of aliphatic-substituted benzenes to produce trimellitic acid. A Delta E color of below 2 is often specified for trimellitic anhydride used in white or transparent resins, and a metal Q content of less than about 50 p.p.m. (parts per million) is desirable to achieve good color and oxidation stability. While the more commonly employed maleic and phthalic acid anhydrides are readily prepared by thermal dehydration of the corresponding acids, and the anhydrides are easily purified by atmospheric pressure sublimation, trimellitic anhydride cannot be processed in this manner. Firstly, the acid requires temperatures in excess of 200° C. for thermal dehydration to take place, and even at these temperatures dehydration is not complete. Secondly, Q trimellitic anhydride is essentially nonvolatile and must be distilled at temperatures above 250° C. under vacuums on the order of 10–60 mm mercury absolute to prevent color degradation. Also, to increase the ordinarily slow rate of dehydration, it has previously been proposed to employ chemical dehydrating agents such as acetic anhydride, sulfuric acid, phosphorus pentoxide, or the like to dehydrate the last traces of trimellitic acid before distilling the anhydride. These chemical dehydrating agents are costly to recover and regenerate, and 0 consequently impose an expensive operating burden on existing processes for the purification of trimellitic anhydride. Furthermore, their use in some cases results in the substitution of one impurity for another.

Dimethyl-2,6-naphthalenedicarboxylate is a monomer that can be used to prepare high performance polymeric materials such as polyesters. One such polyester, poly(ethylene-2,6-naphthalate) (PEN), which is suitably prepared by reacting dimethyl-2,6-naphthalenedicarboxylate with ethylene gycol, has exceptional properties making it useful for a variety of applications. Fibers and films made from PEN polyester have improved strength and improved thermal properties relative to other polyester materials. In addition, films made from PEN demonstrate superior resistence to gas diffusion and especially to the diffusion of carbon dioxide, oxygen and water vapor. Due to its exceptional properties, PEN is highly suitable in applications such as food and beverage containers, Q particularly in so called "hot-filled" food and beverage containers, tire cord and magnetic recording tape.

Although PEN is a high performance polyester, its ultimate properties, performance and physical appearance are dependent to a large extent on the purity, including the color, of the dimethyl-2,6-naphthalenedicarboxylate monomer. Therefore, it is important that dimethyl-2,6-naphthalenedicarboxylate used for the preparation of PEN have as high a purity and as low a color as possible. Superior color is a particularly important factor for Q commercial applications because color is an immediately recognizable measure of purity. Impurities in the dimethyl-2,6-naphthalenedicarboxylate can adversely affect polymerization process to which the dimethyl-2,6-naphthalenedicarboxylate is subjected. Additionally, poor color of dimethyl-2,6-naphthalenedicarboxylate may affect the color of PEN.

Accordingly, an object of the present invention is to provide an improved process for preparing high purity trimellitic anhydride from trimellitic acid having a Delta E color below 1.0 and a metal content below 50 p.p.m.

It is also an object of the present invention to provide an improved process for preparing dimethyl-2,6-naphthalenedicarboxylate having improved color.

It has now been discovered that trimellitic anhydride having Delta E color below 1.0 can readily be obtained by treating crude trimellitic anhydride in the presence of activated boric acid followed by fractionation. It has also been discovered that the purity and, in particular, the color of dimethyl-2,6-naphthalenedicarboxylate can be improved by treating crude dimethyl-2,6-naphthalenedicarboxylate with boric acid activated by organic acids or anhydrides, followed by fractionation. Preferred organic acids and anhydrides for activating boric acid are derived from aliphatic hydrocarbons. Prefered anhydrides have about 2 to 8 carbon atoms while preferred acids have 1 to 8 carbon atoms. Most preferred acids and anhydrides include acetic anhydride, acetic acid, propionic acid, propionic anhydride, formic acid, maleic anhydride and 2-ethyl hexanoic acid.

3. Prior Art

In the prior art German Patent Publication 19 48 374, trimellitic acid is treated with boric acid. In our improved process, trimellitic anhydride is treated with activated boric acid of about 200° to about 275° C. and treated with a decreased pressure and distilled under further decreased pressure at a temperature of about 200° to about 275° C.

SUMMARY OF THE INVENTION

Provided is a process for the production of an aromatic ester or aromatic anhydride having improved color, the process comprising treating the aromatic ester or aromatic anhydride with activated boric acid and fractionating the so treated aromatic ester or aromatic anhydride. Preferably said aromatic ester is dimethyl-2,6-naphthalenedicarboxylate and, preferably, said aromatic anhydride is trimellitic anhydride.

DETAILED DESCRIPTION OF THE INVENTION

In a preferred embodiment about 0.1 to about 1.0 weight percent of an activated boric acid is added to trimellitic anhydride. After this boric acid addition, the trimellitic anhydride is fractionated under a decreased pressure of about 25 to about 1 mm Hg, preferably about 10 to about 5 mm Hg at a temperature of about 200° C. to about 275° C.

Crude trimellitic acid may be prepared by the oxidation of various 1,2,4-aliphatic-substituted benzenes by way of several known routes. Chemical oxidizing agents such as nitric acid, chromic acid, potassium permanganate and the like can oxidize a tri-alkylbenzene such as pseudocumene directly to trimellitic acid. Rather than use chemical oxidizing agents, molecular or gaseous oxygen may be employed to effect a liquid phase oxidation of an aliphatic-substituted benzene in the presence of a heavy Q metal oxidation catalyst such as cobalt or manganese. In this manner, 1,2,4-triisopropyl benzene is oxidized to trimellitic acid. Another process involving molecular-oxygen oxidation is the heavy metal-catalyzed liquid phase oxidation of pseudocumene by repeatedly oxidizing one methyl radical to a carboxyl group, esterifying that carboxyl group with a lower alkanol, and oxidizing another methyl radical on the intermediate to another carboxyl group, followed by hydrolysis of the dialkanol ester of trimellitic acid to trimellitic acid. A more direct Q preparation is the one step oxidation of a trialkylbenzene such as pseudocumene with molecular oxygen in an inert liquid medium at about 150° to about 250° C. employing a catalyst comprising, in conjoint presence, a heavy metal oxidation catalyst and bromine. Suitable metal catalysts are selected from metals having atomic numbers of 13, 21-32, 39-51, 57-84 all inclusive, and the actinide earths, and may be added either in elemental form or as a soluble compound such as cobalt chloride, iron acetate, ammonium chromate, manganese acetyl acetonate, or the like. Likewise, bromine may be added as elemental bromine, HBr, sodium bromide, nickel bromide, benzyl bromide, etc. Trimellitic acid yields from the air oxidation of pseudocumene in the presence of a heavy metal oxidation catalyst and bromine are in excess of 120 weight percent.

In another preferred embodiment, about 0.01 to about 5.0 weight percent of an activated boric acid is added to dimethyl-2,6-naphthalenedicarboxylate. After the addition of activated boric acid, the dimethyl-2,6-naphthalenedicarboxylate is distilled or fractionated, preferably under reduced pressure.

Dimethyl-2,6-naphthalenedicarboxylate suitable for purification by the process of this invention can be obtained by any method known for preparing dimethyl-2,6-naphthalenedicarboxylate. Thus, the process of this invention can be used to purify crude dimethyl-2,6-naphthalenedicarboxylate, or dimethyl-2,6-naphthalenedicarboxylate that has been previously purified by some other method or methods.

One known method for preparing dimethyl-2,6-naphthalenedicarboxylate comprises reacting 2,6-naphthalenedicarboxylic acid with excess methanol, preferably in the presence of a catalyst, at an elevated temperature and/or pressure. Suitably, the esteriferation catalyst is sulfuric acid, p-toluene sulfonic acid, methane sulfonic acid or one or more metal-containing catalysts such as, for example, titanium alkoxide, zinc oxide, or molybdenum trioxide. A suitable method for preparing dimethyl-2,6-naphthalenedicarboxylate from 2,6-naphthalenedicarboxylic acid is disclosed in U.S. Pat. No. 4,886,901 to Holzhauer et al., Ser. No. 274,238 filed November 21, 1988, the specification of which is specifically incorporated herein by reference. This patent also teaches a method for preparing 2,6-naphthalenedicarboxylic acid.

Upon preparing dimethyl-2,6-naphthalenedicarboxylate, for example, by the aforementioned esterification of 2,6-naphthalenedicarboxylic acid with methanol, the dimethyl-2,6-naphthalenedicarboxylate is typically purified by one or more purification procedures such as recrystallization or distillation. Distillation is a preferred method for purifying dimethyl-2,6-naphthalenedicarboxylate becase it readily eliminates high boiling impurities such as monomethyl-2,6-naphthalenedicarboxylate and 2,6-naphthalenedicarboxylic acid. The distillation or fractionation is usually conducted at reduced pressure to avoid excessive distillation temperatures. Excessive temperatures cause a deterioration in the color, i.e., an increase in color, and an increase in the levels of impurities. Even at reduced pressure, however, distillation does not provide for dimethyl-2,6-naphthalenedicarboxylate having superior color properties.

In the process of this invention for obtaining dimethyl-2,6-naphthalenedicarboxylate an activated boron compound is added to the dimethyl-2,6-naphthalenedicarboxylate prior to distillation or fractionation. Q This addition of activated boron compound provides for a distilled product having a lower color than is achieved without the addition of the activated boric acid. The activated boric acid is added to dimethyl-2,6-naphthalenedicarboxylate in an amount sufficient to reduce the color of dimethyl-2,6-naphthalenedicarboxylate upon distillation compared to the color of similarly distilled dimethyl-2,6-naphthalenedicarboxylate that was not treated with activated boric acid. Preferably, the amount of activated boric acid added to the dimethyl-2,6-naphthalenedicarboxylate prior to the distillation is about 0.01 to about 5.0 weight percent, more preferably about 0.05 to about 2.5 weight percent. The distillation is preferably a fractional distillation using a suitable fractionating column, however, a simple distillation procedure is also suitable. The distillation may be batch or continuous. The addition of the activated boric acid to the dimethyl-2,6-naphthalenedicarboxylate may be in one stage or in stages, or continuous throughout the distillation. The fractionation or distillation temperature is preferably in the range of abut 190° C. to about 300° C., more preferably 200° C. to about 275° C., wherein the temperature is the temperature of the bottom of the distillation vessel, and preferably at a pressure of about 2.0 to about 100 mm Hg, absolute, more preferably about 4 to about 60 mm Hg, absolute.

Boric acid is activated according to the process of the invention by heating boric acid in the presence of an organic acid or, preferably, an organic anhydride. The amount of organic acid or anhydride, and the duration and temperature of heating is that sufficient to obtain an activated boric acid compound that reduces the color of TMA and dimethyl-2,6-naphthalenedicarboxylate when added to the TMA or dimethyl-2,6-naphthalenedicarboxylate, and the TMA or dimethyl-2,6-naphthalenedicarboxylate is thereafter fractionated or distilled. Preferably, at least a molar excess of organic acid or anhydride is added to the boric acid and, more preferably, at least two moles Q of organic acid or anhydride per mole of boric acid are added for the activation of the boric acid. Solutions of activated boric acid are also suitable. These solutions are prepared by using an excess molar amount of a liquid acid or anhydride for activating the boric acid. Suitably, a solution of activated boric acid is prepared by heating a mixture comprising about 4 to about 10 parts by weight of liquid organic anhydride or liquid organic acid with about 1 part by weight of boric acid to form a solution of activated boric acid. Preferably this mixture Q is heated to the reflux temperature of the organic acid or organic anhydride. This solution of activated boric acid is suitable for addition to TMA or dimethyl-2,6-naphthalenedicarboxylate. Another method of preparing activated boric acid comprises heating a mixture of boric acid and organic acid or organic anhydride, preferably where there is at least one mole of organic acid or organic anhydride, and more preferably at least two moles of organic acid or organic anhydride per mole of boric acid, until the excess organic acid or anhydride is Q distilled from the reaction mixture leaving a typically solid activated boric acid product. Mixtures of organic acids, mixtures of organic anhydride, and mixtures comprising organic acids and organic anhydrides are also suitable for activating boric acid. In a most preferred method for activating boric acid, about four parts by weight acetic anhydride are heated with 1 part by weight boric acid until a clear solution is obtained.

Although this invention has been described as being useful for improving the purity of TMA and dimethyl-2,6-naphthalenedicarboxylate, it is to be understood that the process disclosed herein is suitable for preparing other aromatic esters and aromatic anhydrides, wherein the aromatic ester or aromatic anhydride can be distilled at either atmospheric, superatmospheric or at reduced pressures to effect a purification thereof, for example, the diesters of 1,2-, 1,3-, 1,4-, 1,5-, 1,6-, 1,7-, 1,8-, 2,3-, 2,6- and 2,7- naphthalenedicarboxylic acid, the diesters of terephthalic acid and the diesters of isophthalic acid, and wherein the alcohol portion of the diester has 1 to about 4 carbon atoms.

The specification of U.S. Patent Application 443,564 filed November 29, 1989 is hereby specifically incorporated by reference.

To further illustrate various embodiments of the hereinafter, it being understood that they are illustrative only.

EXAMPLES

Example 1:

Charged 250 grams of crude TMA to a 500 ml feed pot. Batch fractionation was started right away. The batch fractionation unit consisted of a 500 ml single-neck flask for batch feed pot, one (1) inch ID glass column packed with ⅜ inch ceramic saddles with a packing height of 11 inches, over-head vapor line connecting to the product receiver, and a 500 ml three-neck flask for the product receiver. The feed pot was equipped with a magnetic stirring bar for good agitation, a heating mantle for heating, and a thermometer. The packed column, overhead vapor line, and the product receiver were all electrically traced and insulated. Vacuum was pulled from the product receiver through a two-stage dry ice/aceton cold trap.

The fractionator heater was turned on to stabilize the temperatures to the desired level. Vacuum pump was then turned on and maintained at around 5 mm Hg. The feed pot temperature was then further raised to an appropriate fractionation temperature. The product TMA was collected as an over head condensate. The $\Delta E$ color of the TMA product was 2.69.

Example 2:

Charged 250 grams of crude TMA to a feed pot. The run was carried out the same way as described in Example 1 to check the repeatability of fractionation. The resulting product had a $\Delta E$ color of 2.99.

Example 3:

Charged 250 grams of crude TMA to a feed pot along with 1.25 grams of boric acid. Without any delay, the material was batch fractionated following the similar procedure as described in Example 1. The $\Delta E$ color of the TMA product was 1.11. This shows that the addition of boric acid to crude TMA is somewhat effective in improving TMA color.

Example 4

Into a watch glass of suitable size, charged 10 grams of acetic anhydride. Then, added 1.25 grams of boric acid. The mixture was heated to boil off Q acetic anhydride. The dried powder thus obtained was charged to a 500 ml feed pot along with 250 grams of crude TMA. Batch fractionation started immediately following the similar procedure as described in Example 1. The $\Delta E$ of the product TMA was 0.67, showing that an excellent product color can be obtained without heat soak when boric acid is properly activated prior to the treatment.

Example 5

250 grams of crude TMA to a feed pot. Additionally, 1.25 grams of boric acid dissolved in 5 ml of acetic anhydride was added to the feed pot. The Q batch fractionation started immediately following the similar procedure as described in Example 1. The resulting product had a $\Delta E$ color of 1.23. This example illustrates that a mere mixing of boric acid in acetic anhydride does not activate boric acid for TMA color reduction.

Example 6

Charged 12.5 grams of boric acid and 50 ml of acetic anhydride to a 100 ml flask equipped with magnetic stirrer and condenser. The material was heated very gently to the boiling point and held at reflux for 2 hours. Charged 7 grams of the clear solution thus obtained and 250 grams of crude TMA into a 5600 ml feed pot and started batch fractionation immediately following the similar procedure as described in Example 1. The resulting product had a $\Delta E$ color of 0.68.

Examples 7-11

Conducted in a manner identical to Example 6 except that the boric acid was activated with an acid anhydride or acid other than acetic anhydride. The other acids or anhydrides are listed in Table 1, and the ΔE color is given.

TABLE 1

Activation of Boric Acid with Various Acids/Anhydrides

| Example No. | Acid/Anhydride Used to Activate Boric Acid | TMA Color, DELTA E |
|---|---|---|
| 7 | Formic Acid | 0.44 |
| 8 | Propionic Anhydride | 0.87 |
| 9 | Maleic Anhydride | 0.72 |
| 10 | 2-Ethyl Hexanoic Acid | 0.72 |
| 11 | Propionic Acid | 0.91 |

TMA DELTA E Procedure on the Milton Rov Color Scan II

The equipment setup in current use for the DELTA E procedure consists of a Milton Roy Color Scan II colorimeter, an Adds 1010 video monitor, and an IBM Proprinter. The printer is connected in a fashion to simply print out whatever appears on the Adds 1010 video monitor screen.

I. Start-Up Procedure

A. Initialization

During normal operation the instrument is turned on at all times (e.g., both when in use and when not in use). In this state only the LED indicator for the "INITIALIZE" button will be on. The lamp should be turned off when the unit is not being used in order to prolong lamp life. In the event of a power outage/surge the Color Scan needs to be reinitialized. This is accomplished by simply pressing the "INITIALIZE" button (Blue) on the instrument control panel. This procedure will clear all hardware and software flags and will set the microprocessor in default status. This key can be pressed whenever the operator wishes to abort all action and restart. The factory default settings are listed below along with the values used in the TMA DELTA E measurement.

| Default | TMA Setting |
|---|---|
| DF = 1 | DF = 2 |
| IL = 7 | IL = 1 |
| OB = 0 | OB = 0 |
| PR = 1 | PR = 0 |
| PT = 1 | PT = 3 |
| AV = 1 | AV = 1 |
| CR = 1 | CR = 1 |
| SC = 1 | SC = 1 |
| PF = 0 | PF = 1 |
| RF = 0 | RF = 0 |
| WS = 380 | WS = 380 |
| WE = 700 | WE = 700 |
| WI = 10 | WI = 10 |
| CLOW = 70 | CLOW = 40 |
| CHIGH = 130 | CHIGH = 150 |

To determine whether the variables are set to their proper values enter the command "CF" from the Adds Video Monitor. The variables will then be displayed on the screen and will be printed on the printer. To change a value simply type in the variable and the new value (e.g. type in DF=2 and press the return key).

B. Lamp

The lamp should be turned on for at least thirty minutes prior to calibration or performing measurements. To turn on the lamp, either press the "LAMP" (Green) button on the instrument control panel or enter the command "LAMPON" from the Adds Video Monitor. At the end of either command the LED indicator for the lamp on the instrument control panel will be on, indicating the command was carried out. After completing the measurements, the lamp should be turned off by either pressing the "LAMP" (green) button on the instrument control panel or entering the command "LAMPOFF" from the Adds Video Monitor. The LED indicator for the lamp will be off.

C. Calibration

The calibration procedure should be performed every day after the lamp has warmed up. This assures that calculations will be made against absolute values for reflectance measurements and 100% beam balance for transmittance measurements. The reference tile marked "R" and the Sample Tile marked "S" should be placed in their respective ports. Make sure all parameters are correctly set as described in Section A above. Open the transmission compartment and make sure that both the SPIN/SPEX slide and the small Area View Lever are in the "up" position. To calibrate the instrument simply press either the "CALIBRATE" (Yellow) button on the instrument control panel or enter the command "CA" from the Adds Video Monitor. During the calibration process, the LED indicator for the "CALIBRATE" button will be on. Upon completion of the command an asterisk will appear on the Adds Video Monitor screen and the LED indicator for the "CALIBRATE" button will be off.

In general, the instrument must be recalibrated any time the beginning wavelength (WS), the ending wavelength (WE), or the wavelength increment (WI) is changed. If not, a scan format error will be issued. Additionally, the instrument should be recalibrated when the calibration type (SC), the SPIN/SPEX Slide, or the optics are changed.

Example 12

Crude dimethyl-2,6-naphthalenedicarboxylate prepared by the esterification of 2,6-naphthalenedicarboxylic acid using methanol and sulfuric acid as a catalyst was subject to a batch distillation procedure with and without the presence of 2.5 wt % activated boric acid. The boric acid was activated by heating approximately 4 parts (by weight) of acetic anhydride with 1 part (by weight) of boric acid. The acetic anhydride was first heated to approximately 82° C. (180° F.) and the boric acid was slowly added thereto. The temperature of the mixture rapidly increased to 121° C. (250° F.), and the mixture was maintained at that temperature until the mixture was clear. This "solution" of activated boric acid solidified after remaining at room temperature overnight. The distillations were conducted using a distillation pot bottom temperature of approximately 254° C. and at a pressure of approximately 20 mm Hg, absolute. The distillation apparatus consisted of a 1 liter distillation pot equipped with a 34 inch by 1 inch diameter fractionating column filled with Sulzer Laboratory Packing.

YIE measurements, a measure of "yellowness", were used to evaluate the color properties of the distilled dimethyl-2,6-naphthalenedicarboxylate. "Ambient" YIE values for the samples of dimethyl-2,6-naphthalenedicarboxylate were measured on a Gardner XL-835 tri-stimulus colorimeter using quartz sample cells. YIE measurements were taken on a 0.75 gram sample of distilled dimethyl-2,6-naphthalenedicarboxylate dissolved in 25 ml. of chloroform (see ASTM method E-313, "Indexes of Whiteness and Yellowness of Near-White, Opaque Materials"). YIE values referred to as "Air Melt" were similarly measured using distilled dimethyl-2,6-naphthalenedicarboxylate samples that were first maintained at 235° C. for six hours in a glass vessel without excluding air, i.e., the "Air Melt" measurements are an indication of the stability of the dimethyl-2,6-naphthalenedicarboxylate sample to air at elevated temperature.

The results comparing the distillation of crude dimethyl-2,6-naphthalenedicarboxylate conducted with and without activated boric acid are presented in Table 2. These data demonstrate the pronounced decrease in color obtainable by the process of this invention. Both "Ambient" and "Air Melt" YIE values are substantially reduced for the samples produced by the distillation of dimethyl-2,6-naphthalenedicarboxylate containing activated boric acid compared to the YIE values of the samples produced by the distillation of dimethyl-2,6-naphthalenedicarboxylate without the activated boric acid.

For dimethyl-2,6-naphthalenedicarboxylate prepared by the process of this invention, the "Ambient" YIE is preferably below about 0.15, more preferably below about 0.10, and the "Air Melt" YIE is preferably below about Q 0.50, more preferably below about 0.25.

TABLE 2

| Activated Boric Acid | Batch Distillation of Dimethyl-2,6-Naphthalenedicarboxylate | | | | | | |
|---|---|---|---|---|---|---|---|
| | Fraction No. | | | | | | |
| | 1 | 2 | 3 | 4 | 5 | 6 | 7 |
| | No | | | | | | |
| Wt. Fraction (g) | 51.95 | 54.04 | 51.82 | 51.72 | 50.14 | 53.02 | 5.99 |
| % of Feed Wt. | 11.47 | 11.93 | 11.44 | 11.42 | 11.07 | 11.70 | 1.32 |
| Ambient YIE | 0.21 | 0.18 | 0.19 | 0.17 | 0.20 | 0.23 | 0.29 |
| Air Melt YIE | 9.90 | 1.67 | 0.94 | 0.60 | 1.77 | 4.14 | 10.03 |
| | Yes | | | | | | |
| Wt. Fraction (g) | 55.96 | 53.61 | 53.38 | 47.99 | 52.41 | 55.58 | 53.22 |
| % of Feed Wt. | 11.97 | 11.47 | 11.42 | 10.26 | 11.21 | 11.89 | 11.38 |
| Ambient YIE | 0.11 | 0.03 | 0.06 | 0.04 | 0.04 | 0.02 | 0.04 |
| Air Melt YIE | 6.77 | 0.50 | 0.22 | 0.18 | 0.15 | 0.13 | 0.17 |

That which is claimed is:

1. A process for the production of an aromatic ester or aromatic anhydride having improved color, the process comprising treating the crude aromatic ester or aromatic anhydride with activated boric acid and fractionating the so treated aromatic ester or aromatic anhydride.

2. The process of claim 1 wherein said aromatic ester or aromatic anhydride is dimethyl-2,6-naphthalenedicarboxylate.

3. The process of claim 2 wherein the boric acid is activated with an organic hydrocarbon acid or anhydride.

4. The process of claim 2 wherein said boric acid is activated with a $C_1$–$C_8$ aliphatic acid.

5. The process of claim 2 wherein said boric acid is activated with a $C_2$–$C_8$ aliphatic anhydride.

6. The process of claim 2 wherein said boric acid is activated with acetic anhydride.

7. The process of claim 2 wherein said fractionation is carried out at a temperature in the range of about 190° C. to about 300° C. and at a pressure in the range of about 2.0 to about 100 mg Hg, absolute.

8. The process of claim 7 wherein said activated boric acid is present in the dimethyl-2,6-naphthalenedicarboxylate in an amount of about 0.01 weight percent to about 5.0 weight percent based on the weight of the dimethyl-2,6-naphthalenedicarboxylate.

9. The process of claim 1 wherein said aromatic ester is selected from the group consisting of diesters of 1,2-, 1,3-, 1,4-, 1,5-, 1,6-, 1,7-, 1,8-, 2,3-, 2,6- and 2,7-naphthalenedicarboxylic acid, terephthalic acid and isophthalic acid, the alcohol portion of the diester having 1 to about 4 carbon atoms.

10. A process for the production of trimellitic anhydride with improved color, the process comprising treating crude trimellitic anhydride with activated boric acid followed by fractionation at a temperature of about 200° to about 275° C. and a pressure of about 25 to about 1 mm mercury, wherein the boric acid is activated by heating a mixture of boric acid and an organic hydrocarbon acid or anhydride.

11. The process of claim 10 wherein the boric acid is activated with a aliphatic acid or anhydride.

12. The process of claim 8, wherein the boric acid is activated with $C_1$–$C_8$ aliphatic acids.

13. The process of claim 18 wherein the boric acid is activated with $C_2$–$C_8$ aliphatic anhydrides.

14. The process of claim 10 wherein the boric acid is activated with acetic anhydride.

15. The process of claim 10 wherein the boric acid is activated with formic acid.

16. The process of claim 10 wherein the boric acid is activated with propionic acid.

17. The process of claim 10 wherein the boric acid is activated with maleic anhydride.

18. The process of claim 10 wherein the boric acid is activated with propionic anhydride.

19. The process of claim 10 wherein the boric acid is activated with 2-ethylhexanoic acid.

* * * * *

UNITED STATES PATENT AND TRADEMARK OFFICE
CERTIFICATE OF CORRECTION

PATENT NO. : 5,101,050
DATED : Mar. 31, 1992
INVENTOR(S) : Park et al

It is certified that error appears in the above-indentified patent and that said Letters Patent is hereby corrected as shown below:

| Column | Line |
|---|---|
| 1 | line 47, "metal Q content" should read -- metal content -- |
| 1 | line 68, "and O consequently" should read -- and consequently -- |
| 2 | line 19, "Q particularly" should read -- , particularly -- |
| 2 | line 31, "for Q commercial" should read -- for commercial -- |
| 3 | line 32, "heavy Q metal" should read --- heavy metal -- |
| 3 | line 42, "direct Q preparation" should read -- direct preparation -- |
| 4 | line 43, "Q This addition" should read -- This addition -- |
| 5 | line 13, "moles Q of organic" should read -- moles of organic -- |
| 5 | line 23, "mixture Q is heated" should read -- mixture is heated -- |
| 5 | line 34, "is Q distilled" should read -- is distilled -- |
| 5 | lines 58-60, "embodiments of the hereinafter" should read -- embodiments of the present invention several examples are provided hereinafter -- |

UNITED STATES PATENT AND TRADEMARK OFFICE
CERTIFICATE OF CORRECTION

PATENT NO. : 5,101,050
DATED : Mar. 31, 1992
INVENTOR(S) : Park et al

It is certified that error appears in the above-indentified patent and that said Letters Patent is hereby corrected as shown below:

| Column | Line |
|---|---|
| 6 | line 39, "boil off Q acetic" should read -- boil off acetic -- |
| 6 | line 49, "250 grams of" should read -- "Charged 250 grams of -- |
| 6 | line 51, "The Q batch" should read -- The batch -- |
| 7 | line 5, "The Q other" should read -- The other -- |
| 7 | line 25, "Scan II Q colorimeter" should read -- Scan II colorimeter -- |
| 7 | line 44, "pressed Q whenever" should read -- pressed whenever -- |
| 8 | line 13, "the Q measurements" should read -- the measurements -- |
| 8 | line 23, "for Q reflectance" should read -- for reflectance -- |
| 8 | line 63, "of Q approximately" should read -- of approximately -- |
| 9 | line 35, "about Q 0.50" should read -- about 0.50 -- |

Signed and Sealed this

Twenty-eighth Day of September, 1993

BRUCE LEHMAN

*Attest:*

*Attesting Officer*  *Commissioner of Patents and Trademarks*

UNITED STATES PATENT AND TRADEMARK OFFICE
CERTIFICATE OF CORRECTION

PATENT NO. : 5,101,050
DATED : MARCH 31, 1992
INVENTOR(S) : PARK et al.

It is certified that error appears in the above-indentified patent and that said Letters Patent is hereby corrected as shown below:

| Col. | Line | |
|------|------|---|
| 9 | 55 | "treating the crude aromatic ester" should read --treating the aromatic ester--. |
| 10 | 32 | "treating crude trimellitic" should read --treating trimellitic--. |

Signed and Sealed this

Tenth Day of May, 1994

Attest:

BRUCE LEHMAN

Attesting Officer     Commissioner of Patents and Trademarks